(12) United States Patent
Morath et al.

(10) Patent No.: US 6,504,618 B2
(45) Date of Patent: Jan. 7, 2003

(54) METHOD AND APPARATUS FOR DECREASING THERMAL LOADING AND ROUGHNESS SENSITIVITY IN A PHOTOACOUSTIC FILM THICKNESS MEASUREMENT SYSTEM

(75) Inventors: Christopher Morath, Morristown, NJ (US); Andrey Vertikov, Lake Hiawatha, NJ (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 10/092,866

(22) Filed: Mar. 6, 2002

(65) Prior Publication Data

US 2002/0135784 A1 Sep. 26, 2002

Related U.S. Application Data

(60) Provisional application No. 60/305,226, filed on Jul. 13, 2001, and provisional application No. 60/277,818, filed on Mar. 21, 2001.

(51) Int. Cl.[7] .............................................. G01B 11/06
(52) U.S. Cl. ........................................ 356/630; 356/632
(58) Field of Search ................................. 356/630–632

(56) References Cited

U.S. PATENT DOCUMENTS

| | | | |
|---|---|---|---|
| 4,710,030 A | 12/1987 | Tauc et al. | 356/432 |
| 5,379,109 A | 1/1995 | Gaskill et al. | 356/445 |
| 5,546,811 A | 8/1996 | Rogers et al. | 73/800 |
| 5,693,938 A | 12/1997 | Marchman et al. | 250/234 |
| 5,748,318 A | 5/1998 | Maris et al. | 356/381 |
| 6,008,906 A | 12/1999 | Maris | 356/432 |

Primary Examiner—Frank G. Font
Assistant Examiner—Amando Merlino
(74) Attorney, Agent, or Firm—Harrington & Smith, LLP

(57) ABSTRACT

Disclosed are methods and apparatus for reducing thermal loading of a film disposed on a surface of a sample, such as a semiconductor wafer, while obtaining a measurement of a thickness of the film in an area about a measurement site. The method includes steps of (a) bringing an optical assembly of the measurement system into focus; (b) aligning a beam spot with the measurement site; (c) turning on one of a dither EOM or a dither AOM or a piezo-electric dither assembly to sweep the beam spot in an area about the measurement site, thereby reducing the thermal loading within the measurement site; (d) making a measurement by obtaining a signal representing an average for the film under the area; (e) recording the measurement data; and (f) analyzing the measurement data to determine an average film thickness in the measurement area.

25 Claims, 7 Drawing Sheets

METHOD AND APPARATUS FOR DECREASING THERMAL LOADING AND ROUGHNESS SENSITIVITY IN A PHOTOACOUSTIC FILM THICKNESS MEASUREMENT SYSTEM

CROSS-REFERENCE TO RELATED APPLICATIONS

This application claims priority under 35 USC §119(e) on U.S. provisional patent application Nos. 60/277,818, filed Mar. 21, 2001 and 60/305,226, filed Jul. 13, 2001, which are hereby incorporated by reference in their entireties.

BACKGROUND OF THE INVENTION

1. Field of the Invention

This invention relates generally to optical metrology methods and apparatus and, more particularly, relates to method and apparatus for using light to examine and characterize integrated circuit substrates and devices.

2. Brief Description of Background

The increasing sophistication of semiconductor technology has resulted in a significant shift away from aluminum as the dominant metal in multi-level metallization processes. Copper has been proven to be a suitable metal to use for the metallization, in limited production volumes, and is likely to increasingly become the metal of choice. The differences between aluminum and copper present unique challenges and opportunities for manufacturers of metrology systems, and the manufacturer of metrology equipment that can establish the greatest value early in the implementation of copper based metallization processes is likely to dominate that segment of the market.

Presently, there are several methods for depositing thin films of copper for back end of the line (BEOL) metallization processes. The dominant method currently involves depositing a seed layer of copper on top of a barrier metal such as tantalum, then electroplating a thick layer of copper on top of the seed layer. Once deposited, it is important to be able to verify that the deposited copper is within specifications. What is needed is a way to measure e the thickness of copper films.

The traditional method for measuring the thickness of copper films is the four-point probe method. With this technique, originally developed in the 1950s, an array of four pointed probes arranged in a straight line is pressed into the conductive film. Current is applied to one outer probe, and returned via the opposite outer probe. A measurement of the volt age between the middle two probes is combined with the amount of current and knowledge of the bulk resistivity of the film to determine the thickness of the film. However, this method requires that the probes penetrate the surface of the conductive layer. Doing so causes scratches, and can also cause small amounts of particulates to form that can cause defects elsewhere on the wafer. Additionally, this method requires a priori knowledge of the bulk resistivity of the film. The bulk resistivity depends in part on the grain structure and orientation of the grains in the metal, and a problem that has challenged process engineers working on copper metallization processes is that the grain structure and orientation of the grains in copper changes as a function of time, even if the metallized wafers are left at room temperature. What is thus needed is a non-contact way to measure metal films.

One known type of optical metrology system used for measuring thickness employs a process that involves focusing two pulsed laser beams onto a spot of approximately 1 to 50 microns on a sample. One beam delivers a pulse of energy that induces stress near the surface of the sample. The stress propagates as an acoustic wave away from the sample surface and is partially reflected back towards the surface when it encounters the film/substrate interface or an interface with an underlying film. The second light pulse, time-delayed relative to the first, senses the stress when it reaches the surface via the stress-induced change in the sample's optical properties (e.g. optical reflectance). Analysis of the change in reflectance as a function of time yields accurate measurements of the thickness of each layer in the sample. However, surface roughness causes the measured thicknesses to become position sensitive, i.e., shifting the beams just a few microns can produce significant changes in the measured thicknesses. What is needed is a way to accurately measure film thicknesses where the surface is rough.

Increasing the area over which measurements are made by defocusing one or both beams allows the signal to be averaged over a wider area. For modest amounts of surface roughness, defocusing can work. However, defocusing increases the measurement area, and since the acoustic signal decreases in proportion to the square of the beam diameter, the signal to noise ratio (S/N) degrades accordingly. What is needed is a way to increase measurement area without excessively degrading the acoustic signal.

Increasing the number of measurements within a small neighborhood of a desired measurement site and averaging the thickness results allows the effect of surface roughness to be averaged. However, such an approach significantly increases the total measurement time (by the number of measurements per site), which can significantly reduce throughput. A related approach involves increasing the number of measurements in the neighborhood of a measurement site, but averaging the raw data prior to determining layer thicknesses. Although this approach significantly reduces the measurement time compared to the above-mentioned approach, it still requires a significant amount of time to acquire the raw data. What is needed is a way to overcome measurement sensitivity to spatial variations without adversely affecting measurement throughput.

Furthermore, when using existing metrology systems measurements in any given location depend on the surface roughness of the film. Thus, measurements made in approximately the same region will differ solely due to the roughness of the surface. Multiple measurements decrease throughput, and if only a few measurements are made it is unclear which measurement value best represents the film being measured. What is needed is a way to increase the repeatability of measurements made on rough surfaces.

Vibrating the sample is another approach that can be used to overcome measurement sensitivity to spatial variations. In this approach, a mechanical displacement transducer, e.g., a piezoelectric transducer, is attached to the mechanical assembly on which the sample is placed. Energizing the displacement transducer appropriately causes the sample and the associated measurement location to move. However, there is a relatively low upper limit to the amplitude of vibrations to which a sample can be driven due to the mass of the sample and the sample mounting stage. For displacement amplitudes in the range of tens to hundreds of microns, the measurement frequency is limited to less than 10 Hz by the mass, shape, and resonance frequencies of the sample and sample holder. In addition, mechanically vibrating the sample causes the rest of the measurement stage to vibrate, thus introducing noise to the rest of the system. What is needed is a way to overcome measurement sensitivity to spatial variations without adding mechanical noise to the system.

Increasing the laser beam intensities to enhance the signal to noise ratio causes local heating as a result of optical absorption of successive laser pulses, which in turn causes local annealing. Ideally, the measurement is non-destructive, and to the extent that thermal loading affects the wafer being tested, the measurement is not non-destructive. What is needed is a way to decrease thermal loading. If the pump and probe laser beams can be diverted to a different spot on the sample in a time frame shorter than the occurrence of significant thermal build-up, the non-destructiveness of the measurements can be maintained. For samples having low thermal conductivity or thick layers underneath, this time scale may be on the order of 10–100 laser pulses, thus for a laser with 80 MHz repetition rate a deflection frequency in the range of 1–10 MHz might be necessary to avoid thermal build up.

Photoacoustic systems for measuring the thickness of layers in a film stack on a substrate are well known. Also well known are the use of electro-optic modulators (EOMs) and acousto-optic modulators (AOMs), as well as piezoelectric actuators are also known in the art.

The following U.S. Patents are of interest to the teachings of this invention.

U.S. Pat. No. 6,008,906, "Optical method for the characterization of the electrical properties of semiconductors and insulating films", describes a method for characterizing a sample includes the steps of (a) providing a semiconductor material; (b) applying at least one of an electric field, a pulsed or cw light source, a change in temperature and/or a change in pump pulse intensity to the semiconductor material; (c) absorbing pump light pulses in a portion of the semiconductor material and measuring changes in optical constants as indicated by probe light pulses applied at some time t following the absorption of the pump light pulses; and (e) associating a measured change in the optical constants with at least one of a surface charge, dopant concentration, trap density, or minority carrier lifetime.

U.S. Pat. No. 4,710,030, "Optical generator and detector of stress pulses", describes an optical stress pulse generation and detection system for non-destructively measuring physical properties of a sample, which uses a pump beam having short duration radiation pulses having an intensity and at least one wavelength selected to non-destructively generate a stress pulse in a sample and directs the non-destructive pump beam to a surface of the sample to generate the stress pulse. The optical stress pulse generation and detection system also uses a probe radiation beam and guides the probe beam to a location at the sample to intercept the stress pulse. The change in optical constants induced by the stress pulse is detected by observing the probe beam after it intercepts the stress pulse.

U.S. Pat. No. 5,379,109, "Method and apparatus for non-destructively measuring local resistivity of semiconductors", describes an apparatus for non-destructively measuring resistivity of a semiconductor, such as InP, and includes light sources for illuminating a pre-selected portion of the semiconductor with first and second light beams, each of a pre-selected single wavelength, the first light beam operating to excite the semiconductor by photo injecting carriers, and the second light beam bombarding the local portion of the semiconductor with a pre-selected photon energy. The apparatus measures a fractional change in reflectance of the second light beam responsive to the first light beam, and records this fractional change in reflectance for various values of photon energy of the second light beam, to generate a photoreflectance line-shape. The photoreflectance line-shape is used to calculate a photoreflectance line-shape phase angle, which is used to determine the resistivity of the pre-selected portion of the semiconductor.

U.S. Pat. No. 5,546,811, "Optical measurements of stress in thin film materials", describes a method for determining the residual stress in an unsupported region of a thin film. The method includes the steps of (a) optically exciting the film with a spatially and temporally varying optical excitation field to launch counter-propagating acoustic modes along at least one wave vector; (b) diffracting a portion of an optical probe field off the excited acoustic modes to generate a time-dependent signal field at the excitation wave vector; (c) detecting the signal field to generate a time-dependent, light-induced signal; (d) analyzing the light-induced signal to determine the frequencies of the acoustic modes; (e) partially determining the dispersion of at least one mode; and, (f) comparing the measured dispersion to that calculated using a mathematical model to allow the residual stress properties of the unsupported region of the film to be determined.

U.S. Pat. No. 5,693,938 "Optical probe microscope having a fiber optic tip that receives both a dither motion and a scanning motion, for nondestructive metrology of large sample surfaces", describes an optical probe microscope that includes an optical fiber oriented in a vertical direction. The fiber has a tip that emits light onto a horizontal surface of a sample to be measured. This surface can have both desired and undesired departures from planarity. An electromechanical device for imparting dither motion to the fiber tip is superposed on another electromechanical device for imparting two-dimensional horizontal scanning motion to the fiber tip. The dither motion has a much higher frequency than that of the scanning motion. Between successive scans, another device moves the sample itself from one horizontal position to another. A microscope receives the optical radiation either transmitted or reflected by the sample surface. The microscope forms a (magnified) image of this received optical radiation on the surface of an optical image position detector. The surface of this detector has a relatively large area compared with that of the (magnified) image. The resulting electrical signal developed by the detector provides desired information concerning the scanning position of the fiber tip. Also, this electrical signal is processed and fed back to a vertical pusher that maintains desirably constant the distance of the fiber tip from the sample surface.

U.S. Pat. No. 5,748,318 "Improved Optical Stress Generator And Detector" describes a system for the characterization of thin films and interfaces between thin films through measurements of their mechanical and thermal properties. The system can optically induce stress pulses in a film and optically measure the stress pulses propagating within the film. Change in optical transmission or reflection is measured and analyzed to give information about the ultrasonic waves that are produced in the structure.

SUMMARY OF THE INVENTION

A first distinction between the teachings of this invention and the prior art known to the inventor is in providing an apparatus for measuring the thickness of layers in a thin film stack using a photoacoustic measurement system that includes a dither EOM to sweep the measurement spot in an area about a measurement site, and to obtain a signal representing an average for the film stack under the area.

A second distinction between the teachings of this invention and the prior art is in providing an apparatus for measuring the thickness of layers in a thin film stack using a photoacoustic measurement system that includes a dither AOM to sweep the measurement spot in an area about a measurement site, and to obtain a signal representing an average for the film stack under the area.

A third distinction between the teachings of this invention and the prior art is in providing an apparatus for measuring the thickness of layers in a thin film stack using a photoacoustic measurement system that includes a piezoelectric dither assembly to sweep the measurement spot in an area about a measurement site, and to obtain a signal representing an average for the film stack under the area.

A fourth distinction between the teachings of this invention and the prior art is method for determining the average film thickness of an opaque film in an area about a measurement site on a wafer. The method includes steps of: (a) bringing the optical assembly of the measurement system into focus; (b) aligning the beam spot with a measurement site; (c) turning on a dither EOM according to a pre-determined plan; (d) making a measurement; (e) recording the measurement data; and (f) analyzing the measurement data to determine an average film thickness in the measurement area.

A fifth distinction between the teachings of this invention and the prior art is a method for determining the average film thickness of an opaque film in an area about a measurement site on a wafer is a method that includes the steps of: (a) bringing the optical assembly of the measurement system into focus; (b) aligning the beam spot with a measurement site; (c) turning on a dither AOM according to a pre-determined plan; (d) making a measurement; (e) recording the measurement data; and (f) analyzing the measurement data to determine an average film thickness in the measurement area.

A sixth distinction between the teachings of this invention and the prior art is a method for determining the average film thickness of an opaque film in an area about a measurement site on a wafer, where the method includes the steps of: (a) bringing the optical assembly of the measurement system into focus; (b) aligning the beam spot with a measurement site; (c) turning on a piezo-electric dither assembly according to a pre-determined plan; (d) making a measurement; (e) recording the measurement data; and (f) analyzing the measurement data to determine an average film thickness in the measurement area.

The teachings of this invention provide for the use of an electro-optic deflector or an acousto-optic deflector to sweep the measurement spot on the sample surface to decrease thermal loading.

BRIEF DESCRIPTION OF THE DRAWINGS

The foregoing and other aspects of this invention are made more evident in the following Detailed Description of the Invention, when read in view of the following Drawings, wherein.

DETAILED DESCRIPTION OF THE PREFERRED EMBODIMENTS

The teachings of this invention pertain to apparatus and method for moving to precise locations on a semiconductor or other type of wafer and making a measurement of the thickness of layers of thin films on the wafer. The apparatus dithers a laser beam used in a photoacoustic measurement system so that the location of the spot at which beams generated by the photoacoustic measurement system moves in accordance with the dithering applied to the laser beam.

Figure 1:
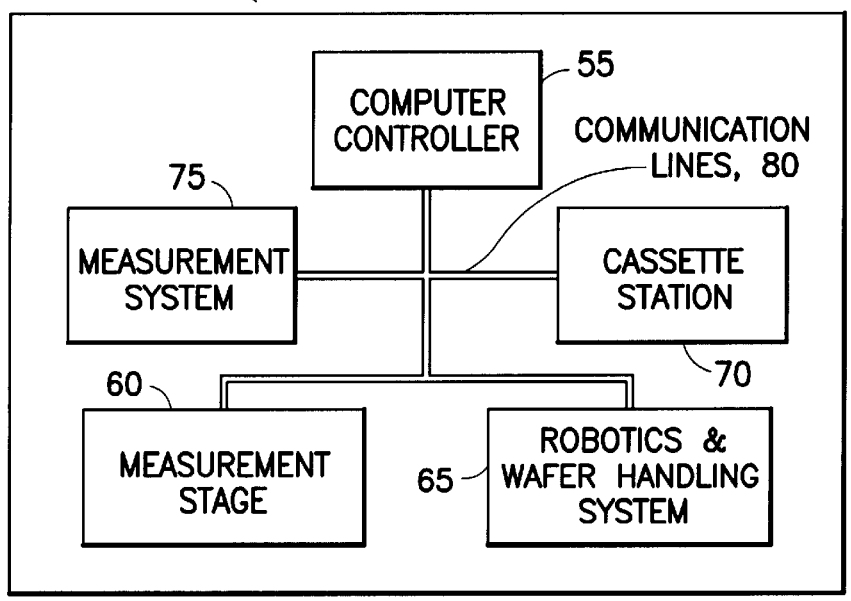
FIG. 1 is a block diagram of an optical metrology system in accordance with these teachings.

FIG. 1 shows a metrology system 50 that includes measurement stage 60, robotics and wafer handling system 65, measurement system 75, cassette station 70, computer controller 55, and communication lines 80. Computer controller (controller) 55 maybe a commonly available personal computer system and is electrically connected to measurement system 75, measurement stage 60, robotics and wafer handling system 65, and cassette station 70 via communication lines 80. Controller 55 further includes software embodied in a computer-readable medium (not shown) capable of carrying out the steps of the present invention.

In operation, controller 55 sends an instruction to the robotics and wafer handling system 65 to extract a wafer from cassette station 70, and to position the wafer on the measurement stage 60. The controller 55 then issues commands to the measurement stage 60 to position the wafer relative to the measurement system so that measurements can be made at a predetermined location. The controller 55 then issues commands to the measurement system 75 to make a measurement and display the results of the measurement. Once the measurement is complete, controller 55 issues instructions to the robotics and wafer handling system 65 to return the wafer to the cassette station 70.

The measurement stage includes a test surface upon which the wafer is placed for measurements, and translation stages to provide wafer manipulation in three degrees of freedom. The preferred embodiment includes two linear stages arranged at right angles with respect to one another and in the plane of the test surface, and another linear stage to move the wafer in the direction of the measurement system.

Figure 2:
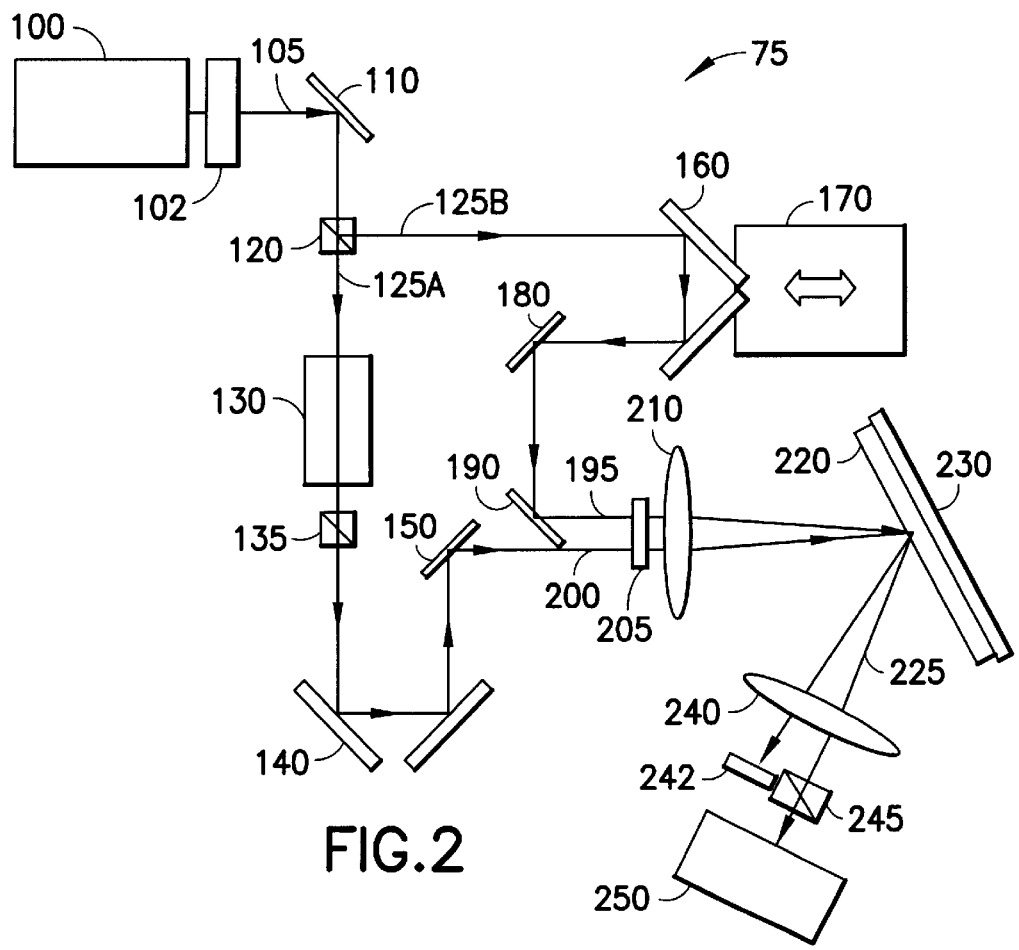
FIG. 2 is a block diagram of a photoacoustic film thickness measurement system wherein the optical paths are illustrated.

FIG. 2 is a schematic diagram of photoacoustic measurement system 75 that includes, as arranged in FIG. 2, a pulsed light source 100, a sample stage 220, a stage/vacuum chuck 230, a first probe steering mirror 180, a pump beam steering mirror 150, a first steering mirror 110, a pump-probe beamsplitter 120, a polarizer 135, and an electro-optic modulator (EOM) 130. Additionally, photoacoustic system 75 includes a probe retroreflector 160, a delay scanning stage 170, a dither EOM 205, a beam dump 242, and a detector 250. Furthermore, photoacoustic measurement system 75 includes a linear pump-discriminating polarizer 245, a harmonic generator wavelength selector (wavelength selector) 102, a projecting lens 210, a collimating lens 240, a pump retroreflector 140, and a second probe steering mirror 190.

Pulsed light source 100 is preferably a titanium-sapphire laser operating at 80 MHz and emitting light at 800 nm. The laser can also be alternatively configured with a frequency doubling birefringent crystal to emit laser beam 105 at 400 nm. Other types of lasers operating with different wavelengths and different frequencies can be used as well.

In operation, pulsed light source 100 emits laser beam 105 that is re-directed by first steering mirror 110. Pump probe beamsplitter 120 splits incident laser beam pulse (preferably of picosecond or shorter duration) into pump beam 125A and probe beam 125B. Electro-optic modulator (EOM) 130 rotates pump beam 125A polarization between horizontal and vertical at a frequency of, for example, 10 kHz to 10 MHz. Polarizer 135 converts pump beam 125A polarization rotation into an amplitude-modulated pump beam 200. Pump retroreflector 140 and pump beam steering mirror 150 deflect modulated pump beam 200 onto dither EOM 205.

A probe beam 125B is transmitted to probe retroreflector 160 where delay scanning stage 170 is used to modify the length of the beam path of probe beam 125B relative to the length of modulated pump beam 200, thus forming time delayed probe beam 195. Delayed probe beam 195 and modulated pump beam 200 propagate through dither EOM 205 and then through projecting lens 210 and finally onto sample 220. Stage/vacuum chuck 230 acts as a positioning unit for the sample wafer and is preferably a multiple-degree of freedom stage that is adjustable in height (z-axis), position (x and y-axes), and tilt (T), and allows motor controlled positioning of a portion of the sample relative to the modulated pump beam 200 and delayed probe beam 195. The z-axis is used to translate the sample vertically into the focus region of the pump and probe beams, the x and y-axes translate the sample parallel to the focal plane, and the tilt axes adjust the orientation of the sample 220 to establish a desired angle of incidence for the probe beam.

Modulated pump beam 200 and delayed probe beam 195 propagate through collimating lens 240 where the modulated pump beam 200 is gathered by beam dump 242. Pump-discriminating polarizer 245 isolates reflected probe beam 225 from the modulated pump beam 200. Detector 250 converts reflected probe beam 225 into a signal versus delay stage 170 position. This signal is demodulated and sent to controller 55 (shown in FIG. 1) for analysis (e.g. to determine film thickness).

Presently preferred techniques for performing the analysis to determine film thickness, as well as to determine other film characteristics, can be found in the following U.S. Pat. No.: 4,710,030, "Optical Generator and Detector of Stress Pulses"; U.S. Pat. No. 5,706,094, "Ultrafast Optical Technique for the Characterization of Altered Materials"; U.S. Pat. No. 5,748,318, "Optical Stress Generator and Detector"; U.S. Pat. No. 5,844,684, "Optical Method for Determining the Mechanical Properties of a Material"; U.S. Pat. No. 5,864,393, "Optical Method for the Determination of Stress in Thin Films"; U.S. Pat. No. 6,008,906, "Optical Method for the Characterization of the Electrical Properties of Semiconductors and Insulating Films"; U.S. Pat. No. 6,025,918, "Apparatus and Method for Measurement of the Mechanical Properties and Electromigration of Thin Films" and U.S. Pat. No. 6,038,026, "Apparatus and Method for the Determination of Grain Size in Thin Films", all of which are incorporated by reference herein in their entireties.

Figure 3:
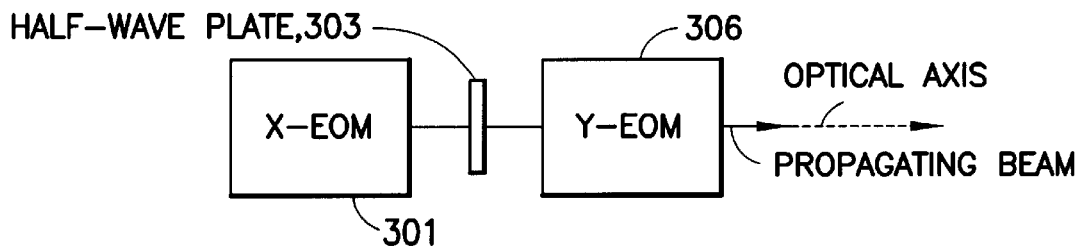
FIG. 3 is a simplified block diagram of a dither electro-optic modulator (EOM)

FIG. 3 shows a schematic diagram of the 2-axis dither EOM. It includes an x-EOM, a half-wave plate, a y-EOM, and a controller/power supply (not shown), all aligned along a common optical axis normal to an x-y plane. The x-EOM includes an electro-optic material such as KDP, and a pair of electrodes mounted on opposite faces transverse to the propagating beam. Voltage applied to the electrodes causes a gradient in the index of refraction proportional to the applied voltage. The gradient in the index of refraction in turn causes the propagating light to be angularly deflected upon exit from the device. The y-EOM is constructed similarly, but is oriented in quadrature to the x-EOM. Thus, application of voltage to the x-EOM causes the beam to be displaced in x-direction, and application of voltage to the y-EOM causes the beam to be displaced in y-direction. One source for a suitable type of dither EOM is Conoptics, Inc. (Danbury, Conn.). The power supply used to drive the x-EOM and the y-EOM is in electronic communication with the controller 55.

Thus, in overall operation (and again referring to FIG. 3), light propagating through the dither EOM is shifted transversally to the optical axis of the dither EOM, and the transverse shift propagates along the rest of the optical path, including the excitation beam path and the probe beam path. Thus, when the beams recombine and impinge upon the sample, they do so at a point displaced from the equilibrium site by an amount dependent upon the displacement of the dither EOM. In practice, the dither EOM is driven by signals in the 10 kHz–20 MHz range, with the x-EOM and the y-EOM being driven by the same frequency, out of phase by 90 degrees so that the beam traces a circle. Other two dimensional driving schemes can be used to cause the beam spot to trace out other patterns, such as a back and forth raster, a serpentine beam spot pattern, a pseudo-random beam spot pattern, etc. A single axis approach can also be used, but this causes the beam to dwell at the endpoints of the motion. The drive amplitude may be adjusted to increase the nominal spot diameter from a fraction of a beam diameter up to approximately 1–10 beam diameters.

In general, one or more of the relative amplitude, the relative phase and the frequencies of the x-excitation and the y-excitation can be varied to cause the beam spot to trace out a desired pattern on the surface of the sample, preferably so as to impinge on a metal or other type of film, or a stack of films, so that the film thickness (and/or some other film characteristic) can be determined from the measured characteristics of the reflected portion of the delayed probe beam 225. This technique beneficially reduces the thermal loading of the film by distributing the laser energy over a wider area, and furthermore beneficially reduces the adverse effects of film surface roughness due to, for example, manufacturing imperfections, grain size, etc. The use of these teachings enables one to accurately represent a film having a grain size and surface features comparable to the beam spot size (e.g., about 10 micrometers), such as a copper film. The film being measured may cover an area that is one or more beam diameters in width, or the film may be of a sub-micron width. The film being characterized may be located in a test area on the substrate, such as a semiconductor wafer, or it may be a portion of an electrical interconnect or a trace or a pad or some other feature normally found on an integrated circuit.

Note that when using the dither EOM 205, or the dither AOM 400 discussed below in relation to FIGS. 3 and 4, the dither rate will typically be much larger than the rate at which the probe beam delay changes with respect to the pump beam. However, it is also within the scope of these teachings to employ a significantly lower dither rate, as when using the piezo-electric dither embodiments discussed below in reference to FIGS. 8, 9, 10, 11 and 12. For example, the beam spot dither or scan rate may be comparable to or less than the rate at which the probe beam delay changes with respect to the pump beam. In this case one is also enabled to perform local imaging of a desired region on the surface of the sample 220. That is, a fine structure imaging technique uses the dither (scanning) mechanism to obtain a map of the local surface area.

Figure 4:
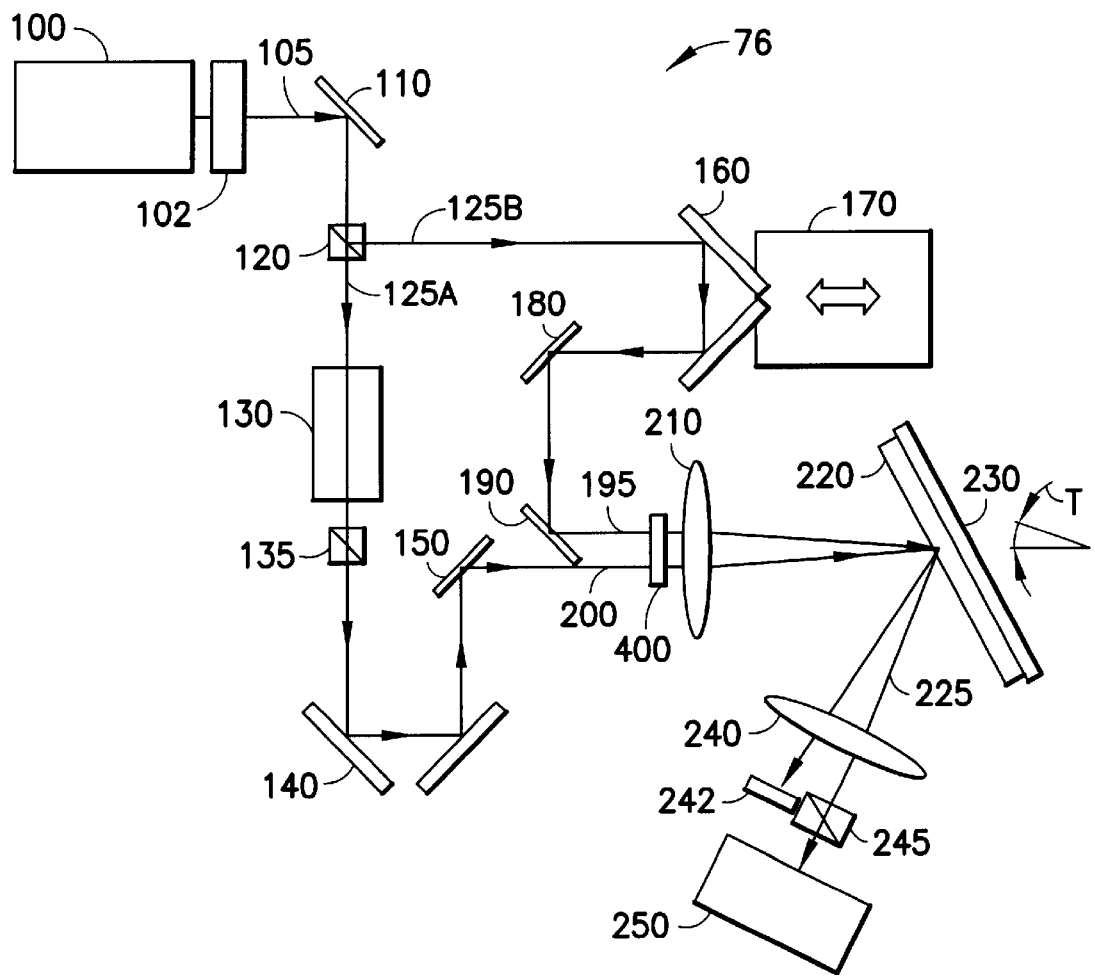
FIG. 4 is a block diagram of a further embodiment of a photoacoustic film thickness measurement system wherein the optical paths are illustrated.

In a second embodiment of the present invention, shown in FIG. 4, a dither AOM 400 is used in lieu of dither EOM 205. Otherwise the schematic is identical to FIG. 2.

Figure 5:
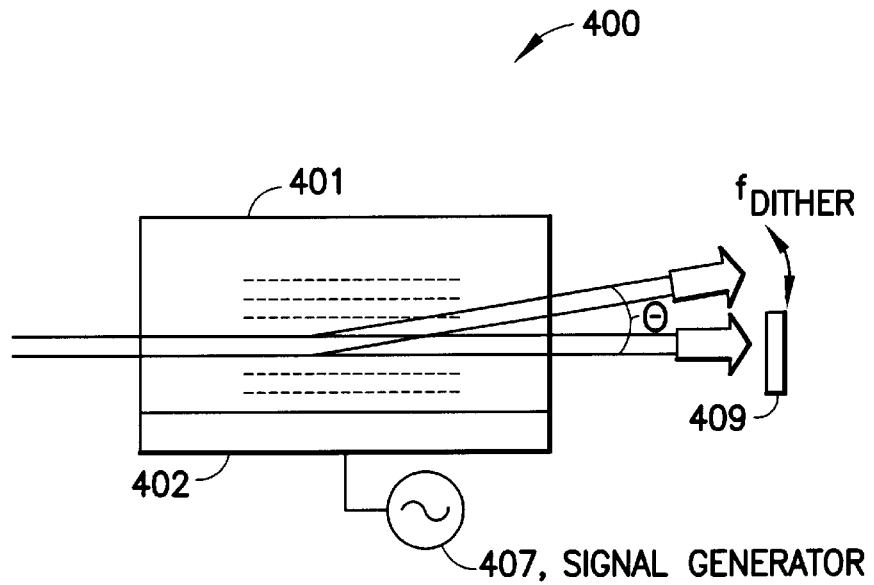
FIG. 5 is an optical schematic of a dither acousto-optic modulator (AOM)

FIG. 5 shows the optical paths through the acousto-optic modulator AOM 400 (single axis). AOM 400 includes an acousto-optic crystal 401, a piezo-electric transducer 402, and a beam dump 409. A double axis deflector has two single axis deflectors oriented in orthogonal directions (one x, one y). AOM 400 includes an acousto-optic crystal 401 functionally connected to a piezo-electric transducer 402. Piezoelectric transducer (transducer) 402 is electrically connected to signal generator 407 and functionally connected to acousto-optic crystal 401. Beam dump 409 is optically connected to AOM 400. Transducer 402 is mounted transversely to the propagating optical beam. Voltage applied to the transducer 402 induces a periodic stress field to form in crystal 401, which causes the optical beam passing through crystal 401 to scatter at a direction θ as shown in FIG. 5. A source for a suitable dither AOM is NEOS Technologies, Inc. (Florida). The signal generator 407 used to drive the AOM is in electronic communication with the controller 55 (shown in FIG. 1).

Figure 6:
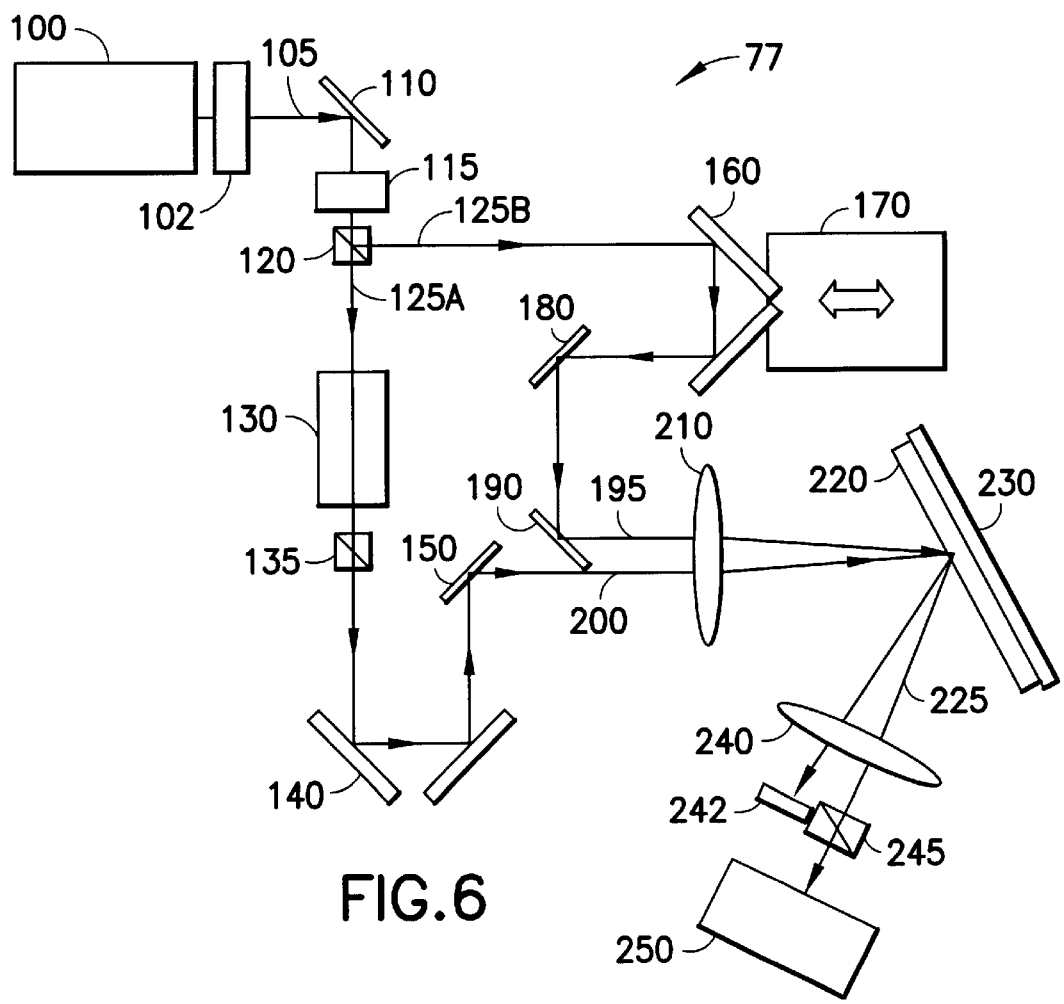
FIGS. 6, 7 and 8 are each a block diagram of a further embodiment of a photoacoustic film thickness measurement system, wherein the optical paths are illustrated.

In operation, delayed probe beam 195 and modulated pump beam 200 pass through dither AOM 400 and are scattered by an angle θ, thus changing the angle of incidence of delayed probe beam 195 and modulated pump beam 200 as they pass through lens 210 and thus the location on sample 220 on which delayed probe beam 195 and modulated pump beam 200 strike. As such, when the beams recombine and impinge upon the sample, they do so at a point displaced from the equilibrium site by an amount dependent upon the displacement of the dither AOM 400. The next embodiment of the photoacoustic film thickness measurement system places the dither assembly prior to pump/probe beamsplitter 115. In this third embodiment of the present invention, shown in FIG. 6, the dither assembly 115 (either EOM or AOM) is used in lieu of dither assembly 205 and is added between the steering mirror 110 and the pump probe beamsplitter 120. Otherwise the schematic is identical to FIG. 2.

Figure 7:
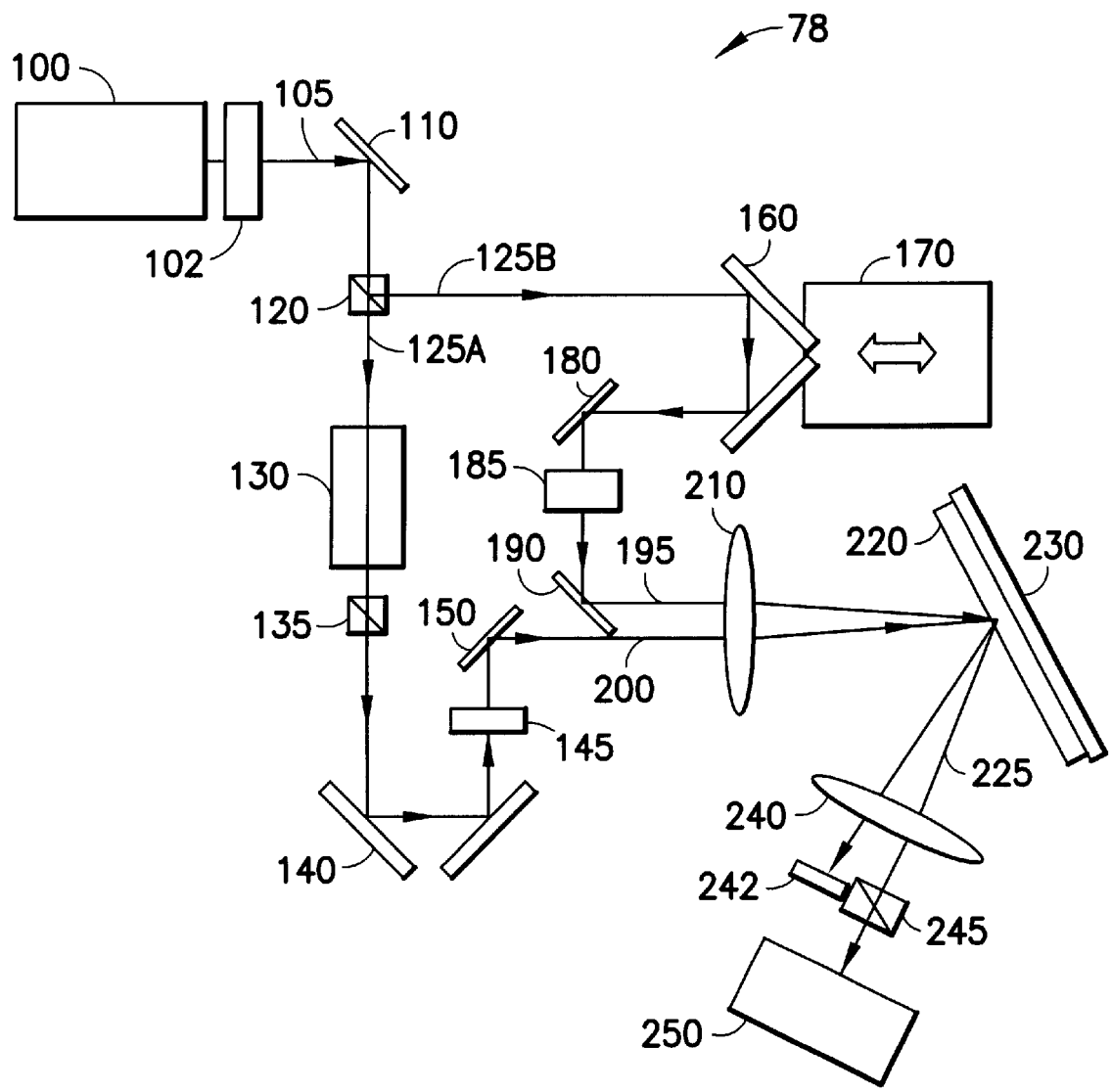

A next embodiment of the photoacoustic film thickness measurement system uses multiple dithering devices (EOM or AOM). In this fourth embodiment of the present invention, shown in FIG. 7, the dithering devices 145 and 185 (either EOM or AOM) are used in place of the dither device 205 shown in FIGS. 2 and 4. Otherwise, the schematic is identical to FIG. 2.

Figure 8:
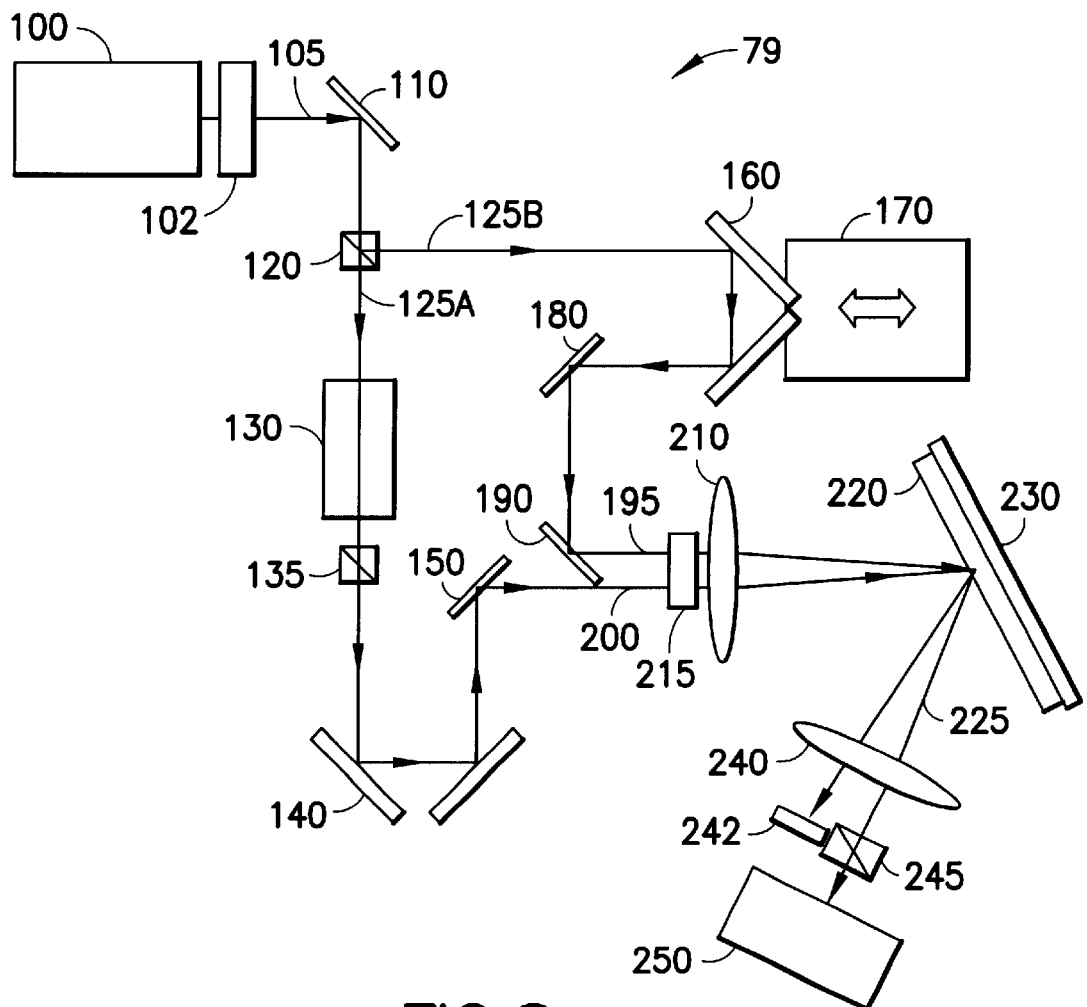

In a next embodiment of the present invention, shown in FIG. 8, piezo-mirror assembly 215 is used in place of the dither EOM 205 shown in FIG. 2. Piezo-dither assembly 215 is located in optical path 195 and optical path 200 prior to projecting lens 210 and sample stage 220. Otherwise, the schematic is identical to FIG. 2.

Piezo-deflection devices of this type have the disadvantage that they are low frequency, typically limited to 1–10 kHz, so the reduction in thermal loading is not significant. However, such devices are simple to employ and are useful for averaging over surface roughness.

Figure 9:
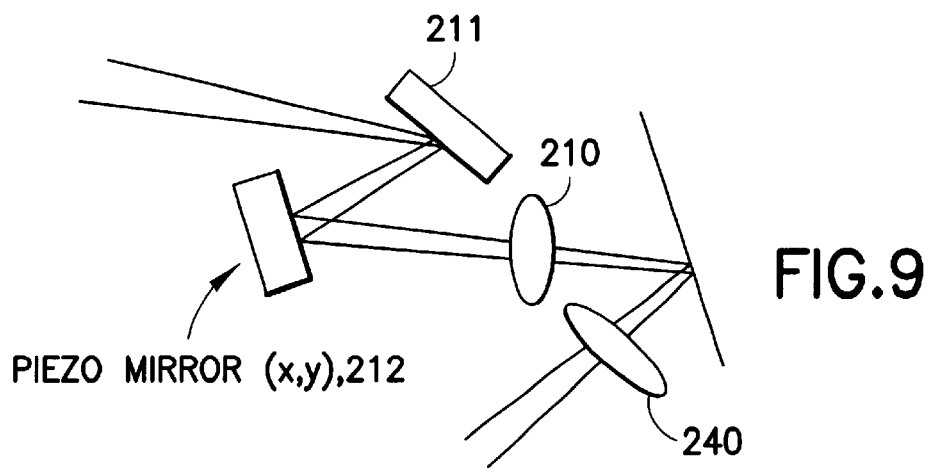
FIG. 9 is an optical schematic of a piezoelectric dither assembly

FIG. 9 shows a portion of the measurement system where a piezoelectric dither system is used to move the beam. Piezoelectric dither assembly 215 includes a folding mirror 211, a piezo mirror 212, a projecting lens 210, and a collimating lens 240. For clarity projecting lens 210 and collimating lens 240 are included to provide context.

Light from the combined probe beam 195 and pump beam 200, as shown in FIG. 2, is incident upon a folding mirror 211, which steers the light toward a piezoelectric mirror assembly 212, from which the light reflects and propagates through the projecting lens 210, which focuses the light on the sample at the measurement site (sample 220, shown in FIG. 2). Light reflected from the sample at the measurement site propagates through collimating lens 240.

Figure 10A:
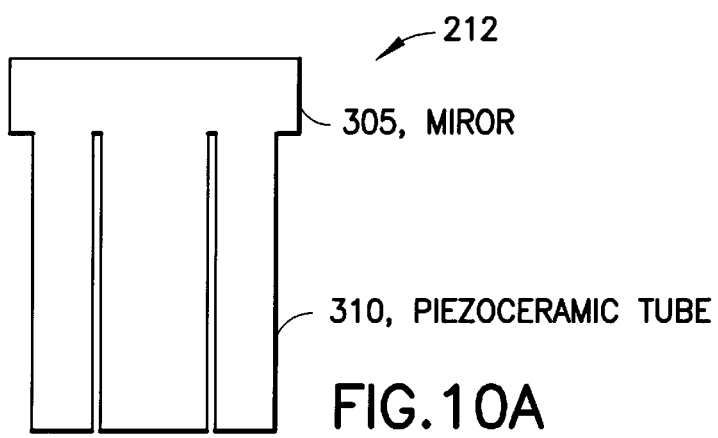
FIGS. 10A and 10B are a top view and a side view, respectively, partly in schematic diagram form, of a piezoelectric mirror assembly.
Figure 10B:
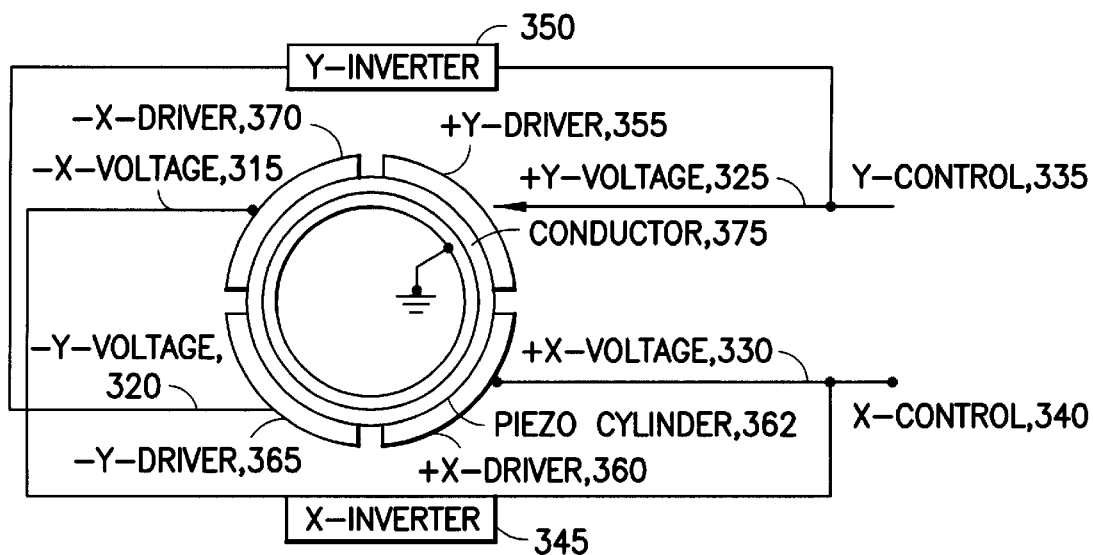

A piezo-mirror assembly 212, shown in FIGS. 10A and 10B, is cylindrical in shape and includes a mirror 305 operatively attached to a piezoceramic tube 310. Piezoceramic tube 310 is formed of a hollow piezoelectric cylinder 362 with an inner and outer surface, where the cylinder is made of piezoelectric material. The inner surface is electrically connected to an electrode, which is connected to ground (as shown in FIG. 10). Four electrodes (+X-driver 360, −X-driver 370, +Y-driver 355, and −Y-driver 365) are electrically connected to the outer surface of the piezoelectric cylinder 362, and are disposed symmetrically around the principle axis of piezoelectric tube 310.

In operation, Y-control signal 335 and X-control signal 340 are control voltages developed by a controller (not shown). +X voltage 330 applied to the +X-driver 360 or −X driver 370 causes that portion of the mirror 305 to move up or down (depending on X-control 340). Likewise, a +Y voltage 320 applied to the +Y-driver 355 or −Y driver 365 causes that portion of the mirror to move up or down (depending on Y-control 335).

Because of the inverters (345 and 350), piezoelectric cylinder 362 deforms symmetrically on opposite sides, thus causing mirror 305 to pivot about an axis perpendicular to the principal axis of mirror 305 and perpendicular to a line connecting the center of opposing drivers.

Figure 11:
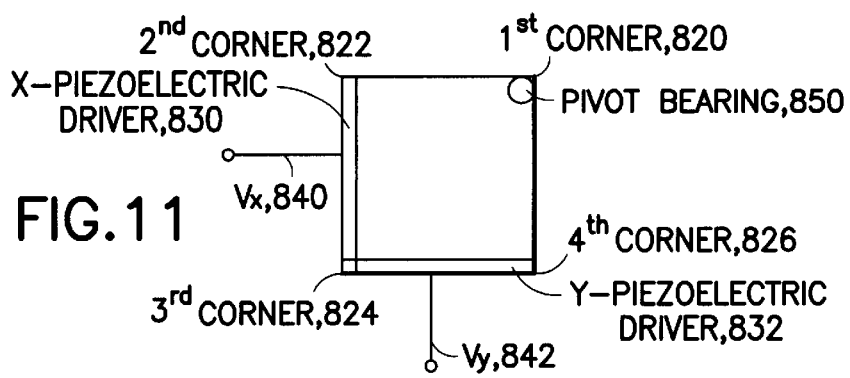
FIG. 11 is a schematic diagram of a piezoelectric dither assembly.

FIG. 11 shows an alternate embodiment of the piezoelectric mirror assembly 805. This embodiment includes a mirror 810 (shown as transparent for clarity in the diagram), an x-piezoelectric driver 830, a y-piezoelectric driver 832, a pivot bearing 850, an x-voltage (Vx 840), and a y-voltage (Vy 842).

The mirror 810 has four sides and four corners. A first corner 820 is positioned above pivot bearing 850. The x-piezoelectric driver 830 is aligned with the side of the mirror 810 between the second corner 822 and the third corner 824. The y-piezoelectric driver 832 is aligned with the side of the mirror 810 between the third corner 824 and the fourth corner 826. The piezoelectric drivers and the pivot bearing 850 are in contact with a reference surface (not shown), and movement of the mirror 810 with respect to the rest of the measurement system is done with respect to the reference surface.

In operation, a voltage Vx 840 applied to the x-piezoelectric driver 830 causes that side of the mirror 810 to move up or down (depending on Vx). Likewise, a voltage Vy 842 applied to the y-piezoelectric driver 832 causes that side of the mirror 810 to move up or down (depending on Vy). Application of voltage Vx 840 induces mirror motion essentially independent from, and transverse to, mirror motion induced by application of the voltage Vy 842.

Although this implementation pertains to the mirror 810 immediately prior to the light hitting the sample, it is understood that the present embodiment applies to any of the other mirrors in the optical path prior to the light striking the sample.

Figure 12:
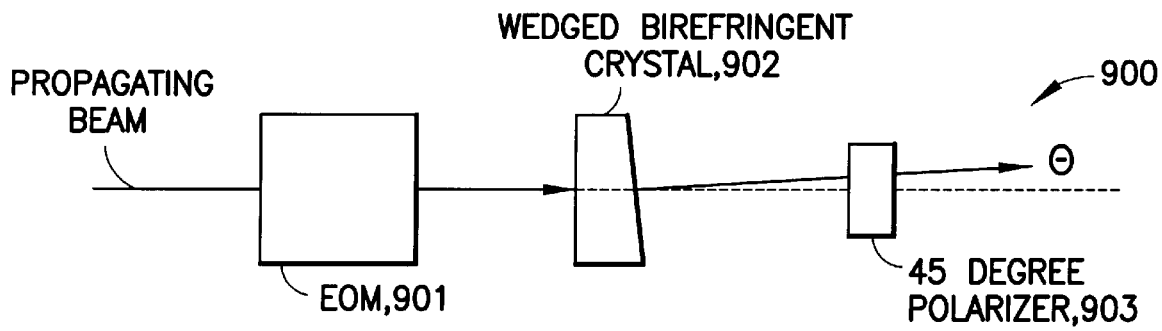
FIG. 12 is an optical schematic of a digital EOM dither assembly.

FIG. 12 illustrates an optical schematic of a digital EOM dither assembly 900. In this embodiment of the present invention, the digital EOM deflector assembly 900 can be used in place of dithering devices 210, 115, 145, as shown in FIGS. 2, 4, 6, and 7. Otherwise, the schematic is identical to FIG. 2.

The two-spot digital deflector 900 includes an EOM phase modulator 901 followed by a wedged birefringent crystal 902 and a polarizer 903. Wedge angle is θ with respect to the fast optic axis of crystal. Exit angle θ varies with polarization according to the index of refraction of the wedge and Snell's law. Since the index of refraction varies with polarization within 902, polarization rotation is converted to a variation in beam output angle θ.

This concept may be extended to a $2^N$-spot digital deflector by placing N deflectors in series. The wedge angles, directions, and EOM driver frequencies and phases may be coordinated to provide the desired deflection pattern for pump and probe beams on the sample.

The operation of the apparatus of the present invention produces a time-dependent signal that may be analyzed using known methods to determine the thickness of one or a plurality of film layers on the sample being measured. The metrology system 50 operates in accordance with these teachings to measure the thickness of layers in a thin film stack, or to measure the thickness of a single layer, using a photoacoustic measurement system that includes, for example, the dither EOM 205, or the dither AOM 400, or the piezoelectric dither assembly 215, or the digital EOM dither assembly 900, to sweep the measurement spot in an area about a measurement site, and to obtain a signal representing an average for the film or film stack under the area.

The metrology system 50 operates to execute a method for determining the average film thickness of an opaque film in an area about a measurement site on a wafer. The method includes steps of: (a) bringing the optical assembly of the measurement system into focus; (b) aligning the beam spot with a measurement site; (c) turning on the dither EOM 205, or the dither AOM 400, or the piezoelectric dither assembly 215, or the digital EOM dither assembly 900, according to a pre-determined plan; (d) making a measurement; (e) recording the measurement data; and (f) analyzing the measurement data to determine an average film thickness in the measurement area.

It is noted that another technique to address the problem that is solved by the teachings of this invention includes inserting an optical cavity (with an unstable mirror configuration to spread the light). However, this approach would increase the complexity of the metrology system 50 substantially above the complexity of the present invention, and would also require sophisticated cavity design to accomplish the benefits realized by the use of the teachings of the present invention.

A second method determines the average film thickness of an opaque film in an area about a measurement site on a wafer and includes: bringing an optical assembly of the measurement system into focus; aligning the beam spot with a measurement site; turning on a dither AOM according to a pre-determined plan; making a measurement; recording the measurement data; and analyzing the measurement data to determine an average film thickness in the measurement area.

Another method for determining the average film thickness of an opaque film in an area about a measurement site on a wafer includes: bringing an optical assembly of the measurement system into focus; aligning the beam spot with a measurement site; turning on a piezoelectric-dither assembly according to a pre-determined plan; making a measurement; recording the measurement data; and analyzing the measurement data to determine an average film thickness in the measurement area.

One difference between these teachings and the prior art is in providing a system and method of operation for determining the average film thickness of an opaque film in an area about a measurement site on a wafer. The method includes: bringing the optical assembly of the measurement system into focus; aligning the beam spot with a measurement site; turning on a dither EOM or a dither AOM or a piezo-dither device or a digital EOM device according to a pre-determined plan or recipe; making a measurement; recording the measurement data; and analyzing the measurement data to determine an average film thickness in the measurement area.

Another difference between these teachings and the prior art is in providing a system and method of operation for reducing thermal loading of the sample by bringing the optical assembly of the measurement system into focus; aligning the beam spot with a measurement site; turning on a dither EOM or a dither AOM or a piezo-dither device or a digital EOM device according to a pre-determined plan for sweeping the beam spot(s); making a measurement and recording the measurement data, where sweeping the beam spot(s) during operation reduces localized heating, and thus maintains the measurement as a non-destructive measurement.

Based on the foregoing teachings it can be appreciated that the use of this invention provides a number of advantages over the conventional approaches discussed above. These advantages include, but need not be limited to, the following. First, the use of these teachings allows stable measurements to be made of samples with rough surfaces. A second advantage that results from the use of these teachings is that repeatable measurements can be made of samples with rough surfaces. A third advantage that results from the use of these teachings is that thermal loading of the sample is suppressed. A fourth advantage that results from the use of these teachings is that the area over which measurements are made is increased. A fifth advantage that results from the use of these teachings is that it permits spatial averaging of film thickness measurements to be accomplished in real time.

Figure 13:
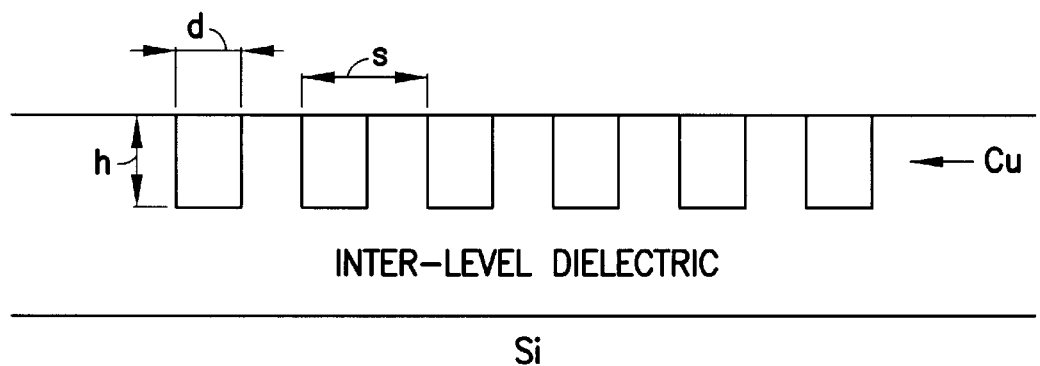
FIG. 13 is a schematic cross-sectional view of a copper line array after deposition and polish.

Reduction of thermal loading is especially critical for opto-acoustic measurements of patterned nano-structures. For example, FIG. 13 shows a cross-section of a Copper (Cu) line array after the Cu deposition and polish. Typical structure dimensions are 0.1–5 microns for the line width d, 0.2–10 microns for the line spacing s, and 1000–30,000 Å for the line thickness h. The Cu is embedded in inter-level dielectric that typically has a thermal conductivity 100–1000 times smaller than the Copper. Thus, the heat generated by the absorbed pump tends to be constrained in the Cu and the temperature rise of the Cu is, in general, larger than for a uniform Cu sample for any given values of the beam intensities.

The use of these teachings provides the benefit of being able to make reliable measurements of film stacks with rough surfaces. Furthermore, there are no moving parts added to the basic metrology system 50 with the preferred embodiment of the present invention.

While described above in the context of presently preferred embodiments, it should be appreciated that these embodiments are not to be construed in a limiting sense upon the practice of this invention.

What is claimed is:

1. An apparatus for measuring the thickness of at least one thin film layer using a photoacoustic measurement system that comprises a dither electro-optic modulator (EOM) to sweep a measurement spot in an area about a measurement site, said measurement spot being comprised of pump beam pulses and corresponding ones of delayed probe beam pulses, further comprising a detector used to obtain, from the delayed probe beam pulses, a signal representing an average signal for the film layer under the area.

2. An apparatus for measuring the thickness of at least one thin film layer using a photoacoustic measurement system that comprises a dither acousto-optic modulator (AOM) to sweep a measurement spot in an area about a measurement site, said measurement spot being comprised of pump beam pulses and corresponding ones of delayed probe beam pulses, further comprising a detector used to obtain, from the delayed probe beam pulses, a signal representing an average signal for the film layer under the area.

3. An apparatus for measuring the thickness of at least one thin film layer using a photoacoustic measurement system that comprises a piezoelectric dither assembly to sweep the measurement spot in an area about a measurement site, said measurement spot being comprised of pump beam pulses and corresponding ones of delayed probe beam pulses, further comprising a detector used to obtain, from the delayed probe beam pulses, a signal representing an average signal for the film layer under the area.

4. A method for determining the average film thickness of an opaque film in an area about a measurement site on a wafer, comprising steps of:
bringing the optical assembly of the measurement system into focus;
aligning the beam spot with a measurement site;
turning on a dither electro-optic modulator (EOM) to sweep the beam spot in an area about the measurement site;
making a measurement by obtaining a signal representing an average for the film under the area;
recording the measurement data; and
analyzing the measurement data to determine an average film thickness in the measurement area.

5. A method for determining the average film thickness of an opaque film in an area about a measurement site on a wafer, comprising steps of:
bringing the optical assembly of the measurement system into focus;
aligning the beam spot with a measurement site;
turning on a dither acousto-optic modulator (AOM) to sweep the beam spot in an area about the measurement site;
making a measurement by obtaining a signal representing an average for the film under the area;
recording the measurement data; and
analyzing the measurement data to determine an average film thickness in the measurement area.

6. A method for determining the average film thickness of an opaque film in an area about a measurement site on a wafer, comprising steps of:
bringing the optical assembly of the measurement system into focus;
aligning the beam spot with a measurement site;
turning on a piezoelectric dither assembly to sweep the beam spot in an area about the measurement site;
making a measurement by obtaining a signal representing an average for the film under the area;
recording the measurement data; and
analyzing the measurement data to determine an average film thickness in the measurement area.

7. A method for reducing thermal loading of a film disposed on a surface of a sample while obtaining a measurement of a thickness of the film, comprising steps of:
bringing a beam spot to a measurement site;
operating a dither assembly to sweep the beam spot in an area about the measurement site, thereby reducing the thermal loading within the measurement site;
making a measurement by obtaining a signal representing an average for the film under the area and recording the measurement data; and
analyzing the measurement data to determine an average film thickness in the measurement area.

8. A method for reducing an effect of surface roughness of a film disposed on a surface of a sample while obtaining a measurement of a thickness of the film, comprising steps of:
bringing a beam spot to a measurement site;
operating a dither assembly to sweep the beam spot in an area about the measurement site;
making a measurement by obtaining a signal representing an average for the film under the area and recording the measurement data, the measurement effectively averaging out the surface roughness of the film; and
analyzing the measurement data to determine an average film thickness in the measurement area.

9. A semiconductor photoacoustic thickness measurement system comprising:
a light source;
a system for creating a modulated pump beam and a delayed probe beam from a laser beam emitted from the light source;
a dither modulator located in paths of both the modulated pump beam and the delayed probe beam to a sample being measured; and
a detector located in a path of a reflected probe beam from the sample,
wherein the dither modulator causes the modulated pump beam and the delayed probe beam to sweep a measurement spot in an area of the sample to obtain an average thickness measurement of the area.

10. A semiconductor photoacoustic thickness measurement system as in claim 9 wherein the dither modulator comprises an electro-optic modulator (EOM).

11. A semiconductor photoacoustic thickness measurement system as in claim 9 wherein the dither modulator comprises an acousto-optic modulator (AOM).

12. A semiconductor photoacoustic thickness measurement system as in claim 9 wherein the dither modulator comprises a piezoelectric dither assembly.

13. A method of determining thickness of a film on a semiconductor substrate comprising steps of:
propagating a modulated pump energy beam and a delayed probe energy beam through a dither modulator;

focusing the beams onto a sample to be measured;

moving a measurement spot of the focused beams in an area of the sample by dithering effect of the dither modulator; and determining an average thickness of the film at the area of the sample from a plurality of thicknesses of the film based upon the beams as reflected off of the sample.

14. A method as in claim 13 wherein the step of moving the measurement spot comprises moving the spot in a circle.

15. A method as in claim 13 wherein the step of moving the measurement spot comprises moving the spot in a back and forth raster.

16. A method as in claim 13 wherein the step of moving the measurement spot comprises moving the spot in a serpentine beam spot pattern.

17. A method as in claim 13 wherein the step of moving the measurement spot comprises moving the spot in a pseudo-random beam spot pattern.

18. A method as in claim 13 wherein the dither modulator comprises a 2-axis dither modulator, and the step of moving the measurement spot comprises moving the beams in orthogonal X and Y directions.

19. A method as in claim 18 further comprising varying at least one of relative amplitude, or relative phase or frequency of an X-excitation and a Y-excitation to trace out a desired pattern on the sample.

20. A method as in claim 13 wherein the dither modulator comprises a dither rate which is larger than a rate at which the probe beam delay changes with respect to the pump beam.

21. A method as in claim 13 wherein the dither modulator comprises a dither rate which is less than a rate at which the probe beam delay changes with respect to the pump beam.

22. A method of performing a photo-acoustic measurement of a patterned structure on a semiconductor substrate comprising steps of:

focusing a pump energy beam and a delayed probe energy beam onto a sample to be measured, the sample comprising a patterned nano-structure within an area to be measured; and during the measurement, dithering a measurement spot of the focused beams within the area to be measured in order to reduce a rise in temperature of the nano-structure.

23. A method as in claim 22, where said patterned nano-structure is comprised of electrical conductors disposed within a dielectric.

24. A method as in claim 22, where said patterned nano-structure is comprised of metal lines disposed within a dielectric, where the dielectric has a thermal conductivity that is at least an order of magnitude less than the metal.

25. A method as in claim 22, where said patterned nano-structure is comprised of an array of structures comprised of copper that is disposed within a dielectric material, where the dielectric material has a thermal conductivity that is at least an order of magnitude less than the copper.

* * * * *